(12) United States Patent
Yorita et al.

(10) Patent No.: US 8,277,731 B2
(45) Date of Patent: Oct. 2, 2012

(54) SENSING DEVICE

(75) Inventors: Tomoya Yorita, Sayama (JP); Junichiro Yamakawa, Sayama (JP); Shigenori Watanabe, Sayama (JP); Mitsuaki Koyama, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 131 days.

(21) Appl. No.: 12/798,936

(22) Filed: Apr. 14, 2010

(65) Prior Publication Data

US 2010/0266451 A1  Oct. 21, 2010

(30) Foreign Application Priority Data

Apr. 16, 2009  (JP) .................. 2009-100397

(51) Int. Cl.
*G01N 33/00*  (2006.01)
(52) U.S. Cl. .................... 422/82; 422/82.01; 422/82.02; 422/68.1; 422/500
(58) Field of Classification Search .................... 422/82, 422/82.01, 82.02, 68.1, 500
See application file for complete search history.

(56) References Cited

U.S. PATENT DOCUMENTS 8,029,741 B2 * 10/2011 Wakamatsu .................. 422/403

FOREIGN PATENT DOCUMENTS

| JP | 11-304752 | 11/1999 |
|---|---|---|
| JP | 2005-164407 | 6/2005 |
| WO | WO 2007/077963 | * 7/2007 |

* cited by examiner

*Primary Examiner* — Sam P Siefke
(74) *Attorney, Agent, or Firm* — Jordan and Hamburg LLP

(57) ABSTRACT

To shorten the time required for an oscillation frequency to stabilize in a sensing device sensing a substance to be sensed by using the fact that a natural frequency of a piezoelectric resonator changes when the substance to be sensed is adsorbed by an adsorption layer formed on the piezoelectric resonator. A sensing device includes: an oscillator circuit 4 oscillating a quartz-crystal resonator 12; and an intense excitation circuit that is formed by the oscillator circuit 4 including a series circuit of a resistor 52 and a third transistor 53 of PNP type and that intensely excites the quartz-crystal resonator 12 connected to the oscillator circuit 4 for a period of time preset by a one-shot circuit 22 by supplying the quartz-crystal resonator 12 with high power equal to or more than twice regular power supplied at the time of the measurement of the substance to be sensed, to stabilize the oscillation of the quartz-crystal resonator 12. When the connection of the quartz-crystal resonator 12 is detected, the one-shot circuit 22 brings the oscillator circuit 4 into an aging state and the high power is supplied to the quartz-crystal resonator 12 to intensely excite the quartz-crystal resonator 12, thereby eliminating the distortion and stress of a quartz-crystal plate 20.

6 Claims, 6 Drawing Sheets

SENSING DEVICE

BACKGROUND OF THE INVENTION

1. Field of the Invention

The present invention relates to a sensing device sensing a substance to be sensed by utilizing the fact that a natural frequency of a piezoelectric resonator changes when the substance to be sensed is adsorbed by an adsorption layer formed on the piezoelectric resonator.

2. Description of the Related Art

Conventionally, as a method of sensing a trace amount of a substance in, for example, a sample solution, there has been known a sensing device using a quartz-crystal resonator which is one of piezoelectric resonators. This sensing device captures antigens by an adsorption layer, for example, an antibody layer, formed on the quartz-crystal resonator by using an antigen-antibody reaction, and evaluates an amount of change in an oscillation frequency of the quartz-crystal resonator as an amount of the captured antigens, that is, as a concentration of the substance to be sensed in the sample solution.

A quartz crystal sometimes has useless distortion or an internal stress, and in this state, the oscillation frequency of the quartz-crystal resonator becomes unstable. Since the sensing device measures the substance to be sensed based on the oscillation frequency unique to the quartz-crystal resonator, the unstable oscillation frequency does not allow the high-precision sensing of the substance to be sensed.

The quartz-crystal resonator has a characteristic that, when it is oscillated, the distortion and internal stress of its quartz-crystal piece gradually disappear and accordingly its oscillation frequency becomes stable. When the quartz-crystal resonator is intensely excited by being supplied with high power equal to or more than twice regular power, preferably, equal to or more than five times regular power and is given a great mechanical vibration, the disappearance of the distortion and internal stress is promoted, so that the oscillation frequency of the quartz-crystal resonator stabilizes in a short time. Therefore, conventionally, before shipping, the quartz-crystal resonator is sometimes subjected to processing in which the quartz-crystal resonator is intensely excited by the supply of high power and thus is given a great mechanical vibration, thereby stabilizing the oscillation frequency of the quartz-crystal resonator. This method, however, has a problem that the effect weakens after two to three months pass.

Further, an oscillator circuit is not capable of supplying high power and not capable of causing the intense excitation of the quartz-crystal resonator since it generally uses a constant current circuit. Therefore, in a conventional sensing device, the oscillation frequency is stabilized by an aging process in which regular power is supplied to cause the gradual disappearance of the distortion and internal stress of a quartz crystal. This method, however, takes a longer time for stabilizing the oscillation frequency of the quartz-crystal resonator than the method of supplying the high power. This method has another problem of low work efficiency since the sensing of a substance to be sensed cannot be performed during this aging process. This has given rise to a demand for a sensing device in which an oscillation frequency can be stabilized in a shorter time.

A patent document 1 describes a holder for electrochemical sensor having a capacitor to which two electrode terminals of a biosensor are connected, and performing the aging after the measurement of the biosensor is finished, whereby an electrolyte surface holds highly stable electric charges and the electric charges are accumulated in the capacitor, so that the state where the electrolyte surface holds the highly stable electric charges is maintained. However, the patent document 1 aims at shortening the time taken for the preparation for the next measurement after the measurement is once finished, and does not give any description regarding the reduction in the time required for the preparation for the measurement when the biosensor is attached to the device. Further, the object of the aging in the patent document 1 is to maintain the state where the electrolyte surface holds the highly stable electric charges and is not the aforesaid disappearance of the distortion and stress of the quartz crystal.

Further, a patent document 2 describes a carbon monoxide sensor that includes a sensor element in which an alumina substrate, a platinum heater, an insulating layer, an oxide catalyst layer, a reference electrode, a solid electrolyte thick film, and a detecting electrode are stacked, and performs aging by applying a higher voltage than a regular voltage to the heater and applying a voltage across the electrodes upon power on, thereby lowering sensitivity to hydrogen gas and improving sensitivity to carbon monoxide. However, the object of the aging in the patent document 2 is to improve the sensitivity to carbon monoxide by applying the voltage and is not the aforesaid disappearance of the distortion and stress of the quartz crystal.

[Patent document 1] Japanese Patent Application Laid-open No. 2005-164407 (paragraph No. 0055, 0056)

[Patent document 2] Japanese Patent Application Laid-open No. Hei 11-304752 (paragraph No. 0023, 0024)

SUMMARY OF THE INVENTION

The present invention was made in consideration of the above circumstances, and has an object to shorten the time required for stabilizing an oscillation frequency in a sensing device that senses a substance to be sensed by utilizing the fact that a natural frequency of a piezoelectric resonator changes when the substance to be sensed is adsorbed by an adsorption layer formed on the piezoelectric resonator.

A sensing device of the present invention is a sensing device which includes a piezoelectric resonator on whose surface an adsorption layer for adsorbing a substance to be sensed is formed and whose natural frequency changes when the substance to be sensed is adsorbed, and senses the substance to be sensed based on the natural frequency of the piezoelectric resonator, the sensing device including:

an oscillator circuit oscillating the piezoelectric resonator; and an intense excitation circuit intensely exciting the piezoelectric resonator connected to the oscillator circuit for a preset period of time by supplying the piezoelectric resonator with high power equal to or more than twice regular power supplied at the time of the measurement of the substance to be sensed, to stabilize the oscillation of the piezoelectric resonator.

In the sensing device of the present invention, for example, the oscillator circuit may serve as part of the intense excitation circuit, and the intense excitation circuit may include a switch part connected to the oscillator circuit and changing power supplied from the oscillator circuit to the piezoelectric resonator between the regular power and the high power. Further, for example, the sensing device of the present invention may further include a time setting part setting the period of time of the intense excitation of the piezoelectric resonator. Further, for example, the sensing device of the present invention may further include an operation screen display part via which the sensing device is operated, and the time setting part may be combined in the operation screen display part. Further, for example, the sensing device of the present invention may further include a connection detecting part detecting the connection of the piezoelectric resonator to the oscillator circuit to output a signal causing the intense excitation circuit to start an intense excitation operation.

According to the present invention, since the intense excitation circuit intensely exciting the piezoelectric resonator connected to the oscillator circuit only for the preset period of time is provided, the piezoelectric resonator is forcibly given a great mechanical vibration, so that the disappearance of distortion and an internal stress of the piezoelectric resonator is promoted and accordingly the time taken for the oscillation frequency of the piezoelectric resonator to stabilize is shortened. This can shorten the time required for an aging process in the sensing device to improve work efficiency. Further, providing the time setting part setting the period of time of the intense excitation enables a flexible operation according to the measurement result, analysis, and the like and makes it possible to prevent the intense excitation from being insufficient or from uselessly lasting for long hours. Further, detecting the connection of the piezoelectric resonator to the oscillator circuit and outputting the signal causing the intense excitation circuit to start the intense excitation operation enable a smooth work, which is convenient.

DETAILED DESCRIPTION OF THE PREFERRED EMBODIMENTS

[First Embodiment]

Figure 1:
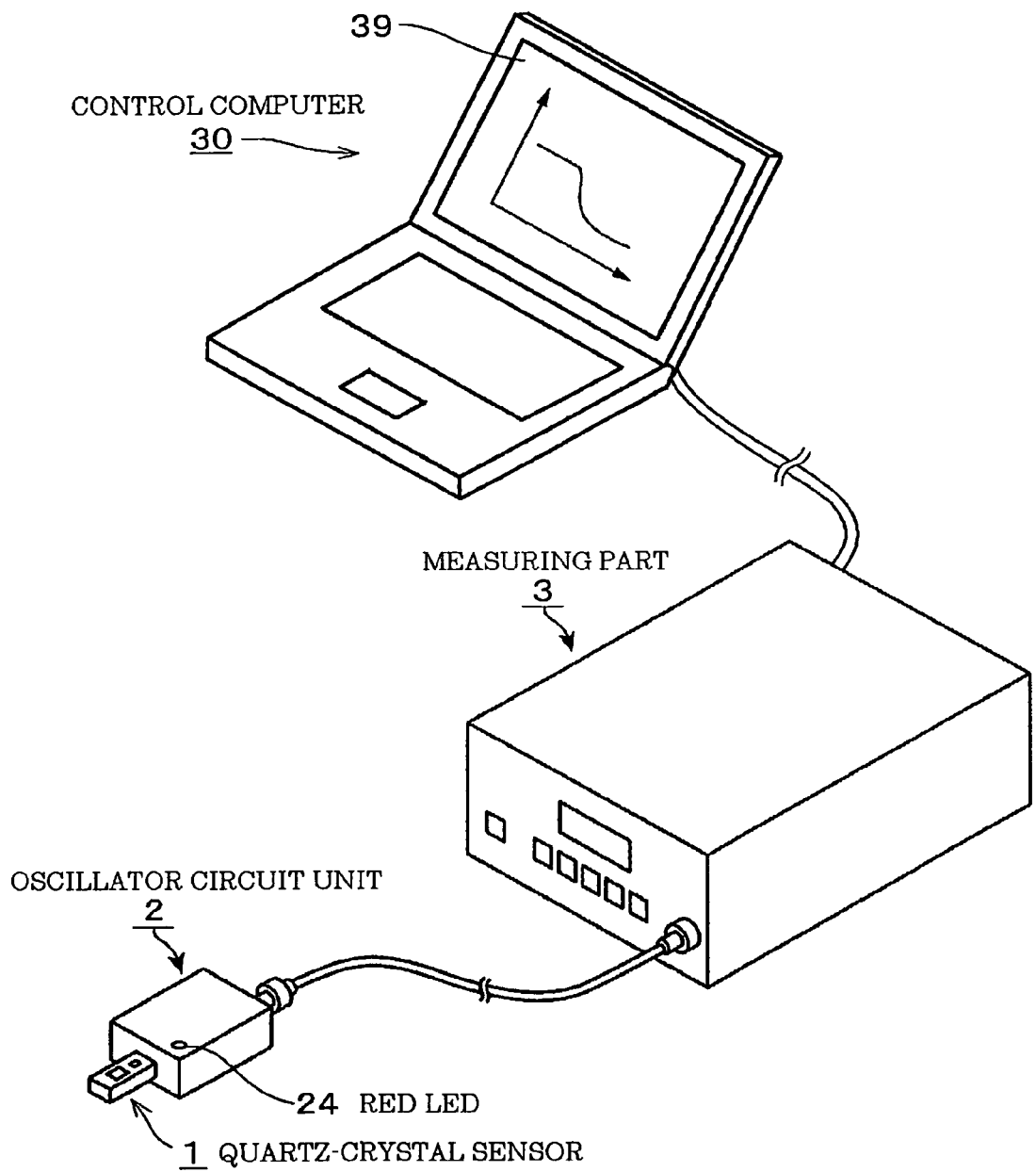
FIG. 1 is a perspective view showing the whole appearance of a sensing device.
Figure 2:
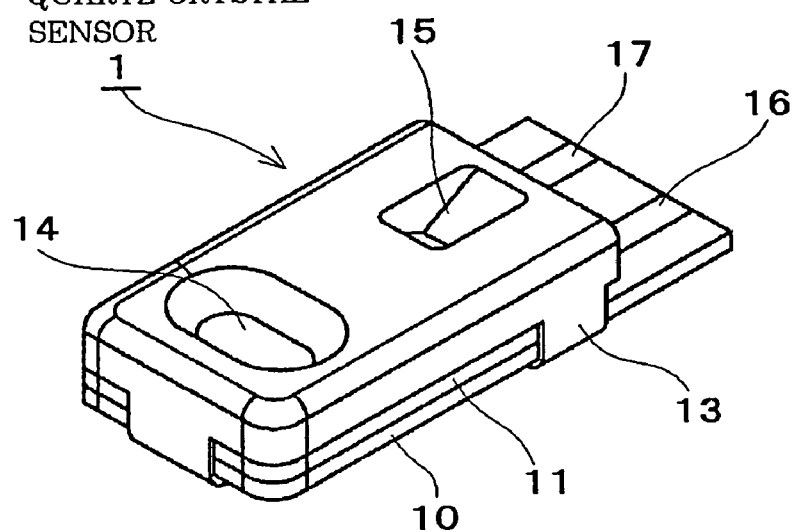
FIG. 2(a) and FIG. 2(b) are explanatory views used to describe an outline of a quartz-crystal sensor.
Figure 2:
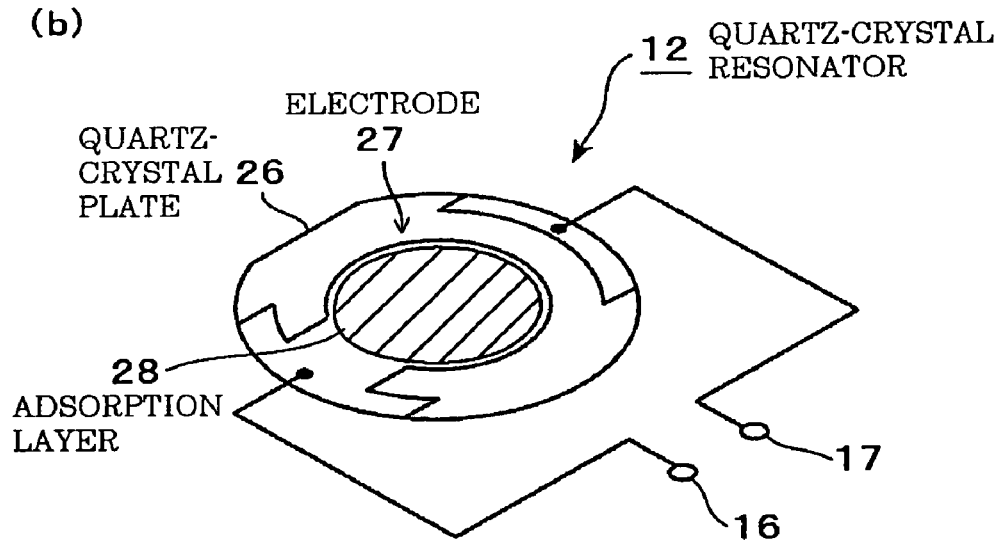

An embodiment of a sensing device of the present invention will be described with reference to FIG. 1 to FIG. 3. As shown in FIG. 1, the sensing device includes: a quartz-crystal sensor 1 supplied with a sample solution containing a substance to be sensed; an oscillator circuit unit 2 to which the quartz-crystal sensor 1 is atachably/detachably connected; a measuring part 3 connected to the oscillator circuit unit 2; and a control computer (hereinafter, referred to simply as a control PC) 30 controlling the oscillator circuit unit 2 and the measuring part 3. The oscillator circuit unit 2 and the control PC 30 are connected to the measuring part 3 via dedicated data cables respectively, and the measuring part 3 receives a frequency signal of the quartz-crystal sensor 1 from the oscillator circuit unit 2 to measure the frequency signal, and transmits the result to the control PC 30.

As shown in FIG. 2(a), the quartz-crystal sensor 1 is composed of a printed circuit board 10 being a wiring board, a rubber sheet 11 stacked on the printed wiring board 10, a quartz-crystal resonator 12 (see FIG. 2(b)), which corresponds to a piezoelectric resonator, provided on the rubber sheet 11, and an upper cover case 13 placed from above the quartz-crystal resonator 12. The quartz-crystal resonator 12 has electrodes 27 provided on both surfaces of a quartz-crystal plate 26 in, for example, a circular shape (the electrode on a rear surface side is not seen), and the electrodes 27 are electrically connected to printed circuits 16, 27 provided on the printed circuit board 10, respectively, by a conductive adhesive or the like. On a front surface side of the electrode 27, an adsorption layer 28 for adsorbing the substance to be sensed is formed. The adsorption layer 28 is made of an antibody for capturing an antigen being a substance to be sensed in the sample solution by an antigen-antibody reaction. Further, a sample solution injection port 14 and a sample solution observation port 15 are formed in the upper cover case 13.

The quartz-crystal sensor 1 is attachable/detachable to/from the oscillator circuit unit 2 as described above by having the printed circuit board 10 inserted/detached thereto/therefrom, and when the quartz-crystal sensor 1 is inserted, the quartz-crystal resonator 12 is electrically connected to an oscillator circuit 4 (see FIG. 3) in the oscillator circuit unit 2 via the printed circuits 16, 17. In the quartz-crystal sensor 1, the sample solution containing the substance to be sensed is injected through the injection port 14 to fill a space on an upper surface side of the quartz-crystal resonator 12 provided in the quartz-crystal sensor 1, and the adsorption layer 28 provided on the quartz-crystal resonator 12 adsorbs the substance to be sensed in the sample solution. Since the adsorption of the substance to be sensed by the adsorption layer 28 causes a change in an oscillation frequency of the quartz-crystal resonator 12, the sensing device senses the substance to be sensed by detecting the change in the oscillation frequency.

Figure 3:
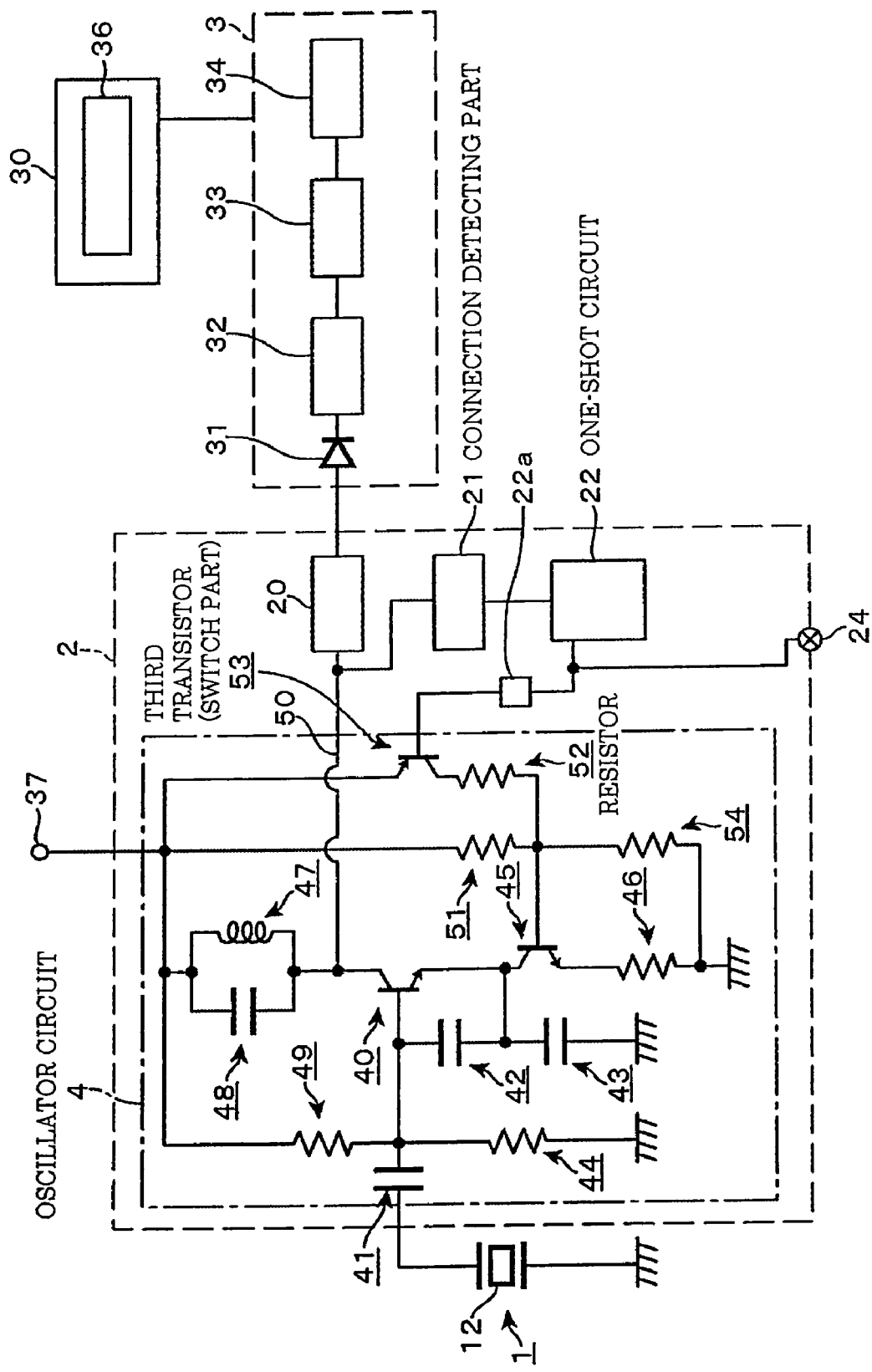
FIG. 3 is a plane view used to describe the whole circuit of the sensing device.

As shown in FIG. 3, the oscillator circuit unit 2 includes: the oscillator circuit 4; a buffer amplifier 20 connected on a subsequent stage of the oscillator circuit 4; a connection detecting part 21 detecting, based on an oscillation output of the oscillator circuit 4, that the quartz-crystal sensor 1 is connected to the oscillator circuit unit 2 to output a pulse; and a one-shot circuit (monostable multivibrator) 22, which corresponds to a time setting part, outputting a pulse with a predetermined pulse width in response to the output pulse of the connection detecting part 21. The connection detecting part 21 outputs the pulse based on a rising edge of the output of the oscillator circuit 4. The one-shot circuit 22 has a function of adjusting the pulse width of the output pulse, and concretely, is capable of adjusting a capacitance value of a variable capacitor of a time constant circuit deciding the pulse width. Further, an inverter circuit 22a inverting the output of the one-shot circuit 22 is connected to an output end from which the one-shot circuit 22 outputs the pulse.

The oscillator circuit 4 is structured as a Colpitts oscillator circuit. As shown in FIG. 3, a first transistor 40 of NPN type serving as an oscillation amplifying element is provided in the oscillator circuit 4, and the quartz-crystal resonator 12 is connected to a base side of the first transistor 40 via a capacitor 41. Further, between the base of the first transistor 40 and a ground, a series circuit of capacitors 42, 43 forming a divided capacitive component is connected, and a midpoint of the capacitors 42, 43 is connected to an emitter side of the first transistor 40. Further, between the base of the first transistor 40 and the ground, a bleeder resistor 44 is provided in parallel to the series circuit of the capacitors 42, 43.

Between the emitter of the first transistor 40 and the ground, a second transistor 45 of NPN type and a resistor 46 forming a positive feedback loop are connected. A power supply terminal 37 supplying +Vcc via a parallel circuit of an inductor 47 and a capacitor 48 is connected to a collector side of the first transistor 40. A base of the second transistor 45 is connected to a midpoint of two series resistors 51, 54 provided between the power supply terminal 37 and the ground, and a constant current circuit is formed by the second transistor 45, the resistor 46, and the series resistors 51, 54. Therefore, at the time of the measurement of the substance to be sensed, a constant current is supplied to the quartz-crystal sensor 1. Note that, in FIG. 3, 49 denotes a bleeder resistor and 50 denotes an output end of the oscillator circuit.

A series circuit composed of a resistor 52 and a third transistor 53 of PNP type is connected in parallel to the series resistor 51, and the third transistor 53 has an emitter side connected to the power supply terminal 37, a collector side connected to the resistor 52, and a base side connected to the one-shot circuit 22. Being intended to increase a base potential of the second transistor 45, the resistor 52 is lower in resistance value than the series resistor 51, and for example, the resistance values of the series resistors 51, 54 and the resistor 52 are 15 kΩ, 10 kΩ), and 0 kΩ respectively.

The third transistor 53 corresponds to a switch part for changing power supplied to the quartz-crystal resonator 12 between regular power and high power for aging. Its role will be briefly described. At a regular time (at the time of the measurement of the substance to be sensed), the third transistor 53 is off, and therefore, the base of the second transistor 45 is supplied with a voltage resulting from the division of a DC voltage of the power supply terminal 37 by the series resistors 51, 54, so that a constant current flows in the second transistor 45. On the other hand, at the time of the later-described aging, the third transistor 53 turns on, and a voltage substantially equal to a voltage resulting from the division of the DC voltage of the power supply terminal 37 by the resistor 52 and the series resistor 54 is applied to the base of the second transistor 45, so that a base voltage of the second transistor 45 increases and as a result, the current in the second transistor 45 increases. Therefore, the oscillator circuit 4 including the series circuit of the resistor 52 and the third transistor 53 of PNP type corresponds to an intense excitation circuit of the present invention.

As shown in FIG. 3, the measuring part 3 includes: a diode 31, an A/D converter circuit 32, and a FGPA (Field Programmable Gate Array) 33 being a signal processing circuit processing a digital signal received from the A/D converter circuit 32, and further includes a CPU 34 controlling the measuring part 3 and controlling data transmission/reception between the oscillator circuit unit 2 and the control PC 30. The control PC 30 includes control software 36 controlling the measuring part 3 and analyzing measurement information received from the measuring part 3.

In the measuring part 3, upon activation, the CPU 34 transmits a control command to the FGPA 33 and so on and notifies the activation to the control PC 30. Then, the measuring part 3 measures the frequency signal received from the oscillator circuit unit 2 to transmit the measurement result to the control PC 30. Further, the control software 36 of the control PC 30 has a function of displaying the received measurement result on a display 39 (see FIG. 1) and a function of determining a state of the one-shot circuit 22 based on the received measurement result to display the determination result on the display 39, so that a user can recognize, on the display 39, a current oscillation frequency of the quartz-crystal resonator 12 and whether or not the pulse is currently output from the one-shot circuit 22 (a later-described aging process state).

Further, in the oscillator circuit unit 2, a red LED 24 notifying that the pulse is being output from the one-shot circuit 22 is provided. As shown in FIG. 3, the red LED 24 is connected to the one-shot circuit 22 side of the inverter circuit 22a, and is kept lighted while the pulse is output from the one-shot circuit 22.

Next, the flow of the measurement of the substance to be sensed in this embodiment will be described. First, the quartz-crystal sensor 1 is attached to the oscillator circuit unit 2 as shown in FIG. 1. Consequently, the quartz-crystal sensor 12 and the oscillator circuit 4 are connected and the frequency signal (oscillation output) is output from the oscillator circuit 4. The connection detecting part 21 detects a rising edge of, for example, input level to output the pulse to the one-shot circuit 22, so that the one-shot circuit 22 supplies the pulse with a preset length to the base of the third transistor 53 via the inverting circuit 22a.

Accordingly, a base potential of the third transistor 53 changes from "H (high level)" to "L (low level)", so that the third transistor 53 turns on. This as a result causes an increase in the base potential of the second transistor 45, then, an increase in a collector-emitter current of the second transistor 45, and then an increase in a base-emitter voltage of the first transistor 40, resulting in an increase in the supply power to the quartz-crystal sensor 1. Hereinafter, the power supplied to the quartz-crystal sensor 1 at this time will be called high power. A value of the high power is equal to or more than twice the power supplied to the quartz-crystal sensor 1 at the time of the measurement of the substance to be sensed (at the regular time), preferably, equal to or more than five times. In this embodiment, as a result of measuring the high power, the value of the high power became ten times the power supplied at the regular time. Further, in the control PC 30, the state where the pulse is output from the one-shot circuit 22, that is, the aging process state, is displayed by the control software 36 on the display 39 being a display part. Further, in the oscillator circuit unit 2 at this time, the red LED 24 is in a lighted state. That is, the state where the high power is applied to the quartz-crystal resonator 12 is displayed on the display 39 and in the oscillator circuit unit 2.

When the high power is supplied to the quartz-crystal sensor 1, the aging process of the quartz-crystal resonator 12 is performed, so that the quartz-crystal resonator 12 is intensely excited. Consequently, the quartz-crystal plate 26 is given a great mechanical vibration and the disappearance is of the distortion and internal stress of the quartz-crystal 26 is promoted, so that the oscillation frequency of the quartz-crystal resonator 23 is stabilized in a short time.

After a period of time corresponding to the set width of the one-shot circuit 22 passes, the pulse from the one-shot circuit 22 disappears and the base potential of the third transistor 53 changes from "L" to "H", so that the third transistor 53 turns off. As a result, the base potential of the second transistor 45 lowers and the constant current decided by the series resistors 51, 54 and the resistor 46 flows between the collector-emitter of the second transistor 45, and the supply power to the quartz-crystal resonator 12 comes to have a value set at the regular time, for example, 3 μW. The display of the aging process state disappears from the display 39, and the red LED 24 is lighted out in the oscillator circuit unit 2.

Upon confirming that the display of "aging process state" has disappeared in the control PC 30 or the red LED 25 has been lighted out, an operator injects pure water or a buffer liquid into the quartz-crystal sensor 1 and finds the oscillation frequency of the quartz-crystal sensor 1 corresponding to what is called a blank value. That is, the frequency signal of the oscillator circuit 4 is input to the FGPA 33 via the buffer amplifier 20, the diode 31, and the A/D converter circuit 32, and the FGPA 33 finds the frequency of the frequency signal. For this measurement of the frequency signal, used is, for example, a method in which a rotation velocity of a rotation vector is found based on a real component and an imaginary component of the rotation vector, the rotation vector being obtained by quadrature detection of a digital signal obtained in the A/D converter circuit 32. Incidentally, a frequency counter may be used for the measurement of the frequency.

After time-series data of the measurement value of the frequency found in the measuring part 3 are taken into the control program 36 of the control PC 30, the operator injects the sample solution containing the substance to be sensed into the injection port 14 of the quartz-crystal sensor 1. When the sample solution containing the substance to be sensed is injected to the quartz-crystal sensor 1, the substance to be sensed in the sample solution is adsorbed by the adsorption layer 28 of the quartz-crystal resonator 12, so that the oscillation frequency of the quartz-crystal resonator 12 lowers according to an adsorption amount of the substance to be sensed.

Then, the measuring part 3 finds a frequency of the frequency signal of the oscillator circuit unit 2 and transmits time series data of the measurement value of the frequency to the control PC 30. In the control PC 30, the time series data of the measurement value of the frequency corresponding to the blank value found when the pure water or the buffer liquid is used and the time series data of the measurement value of the frequency found after the sample solution is injected are displayed, and based on these time series data, the operator or the control program 36 of the control PC 30 finds how much the frequency of the quartz-crystal resonator 12 is lowered by the injection of the sample solution (frequency difference). Then, the concentration of the substance to be sensed in the sample solution is found based on a calibration curve prepared in advance, for instance.

As described above, in the sensing device of this embodiment, the oscillator circuit unit 12 is structured such that the one-shot circuit 22 outputs the pulse for the preset period of time, and based on the pulse, the quartz-crystal resonator 12 of the quartz-crystal sensor 1 connected to the oscillator circuit 4 is intensely excited. Accordingly, a great mechanical vibration is forcibly given to the quartz-crystal resonator 12 to promote the disappearance of the distortion and internal stress of the quartz-crystal resonator 12, which makes it possible to shorten the time required for the oscillation frequency of the quartz-crystal resonator 12 to stabilize. Therefore, the time required for the aging process in the sensing device can be shortened, resulting in improved work efficiency.

Further, since the one-shot circuit 22 can set the period of time of the intense excitation of the quartz-crystal resonator 12, flexible operations such as changing the period of time of the intense excitation by changing the setting according to the measurement result, the analysis, and so on are enabled. Therefore, it is possible to prevent the intense excitation from being insufficient or from uselessly lasting for long hours. Further, since the connection detecting part 21 detects that the quartz-crystal resonator 12 is connected to the oscillator circuit 4 and the quartz-crystal resonator 12 is then intensely excited, the automatic start of the aging process is enabled only by inserting the quartz-crystal sensor 1 into the oscillator circuit unit 2, which enables a smooth work and is convenient.

Further, in this embodiment, from the display on the display 39 and from the red LED 24 provided in the oscillator circuit unit 2, the operator can be informed of the state where the one-shot circuit 22 is outputting the pulse, that is, the state where the high power is supplied to the quartz-crystal resonator 12 and the aging process is underway, which makes it possible to prevent the sample solution from being injected into the quartz-crystal sensor 1 before the aging process is finished. In particular, since the red LED 24 serving as a display part is provided in the oscillator circuit unit 2 to which the quartz-crystal sensor 1 is attached, the display part is provided in the quartz-crystal sensor 1 side, which makes it possible to confirm whether or not the aging is underway, only by checking the red LED 24 when the sample solution is injected, and to prevent the sample solution from being mistakenly injected while the aging process is underway.

[Second Embodiment]

Figure 4:
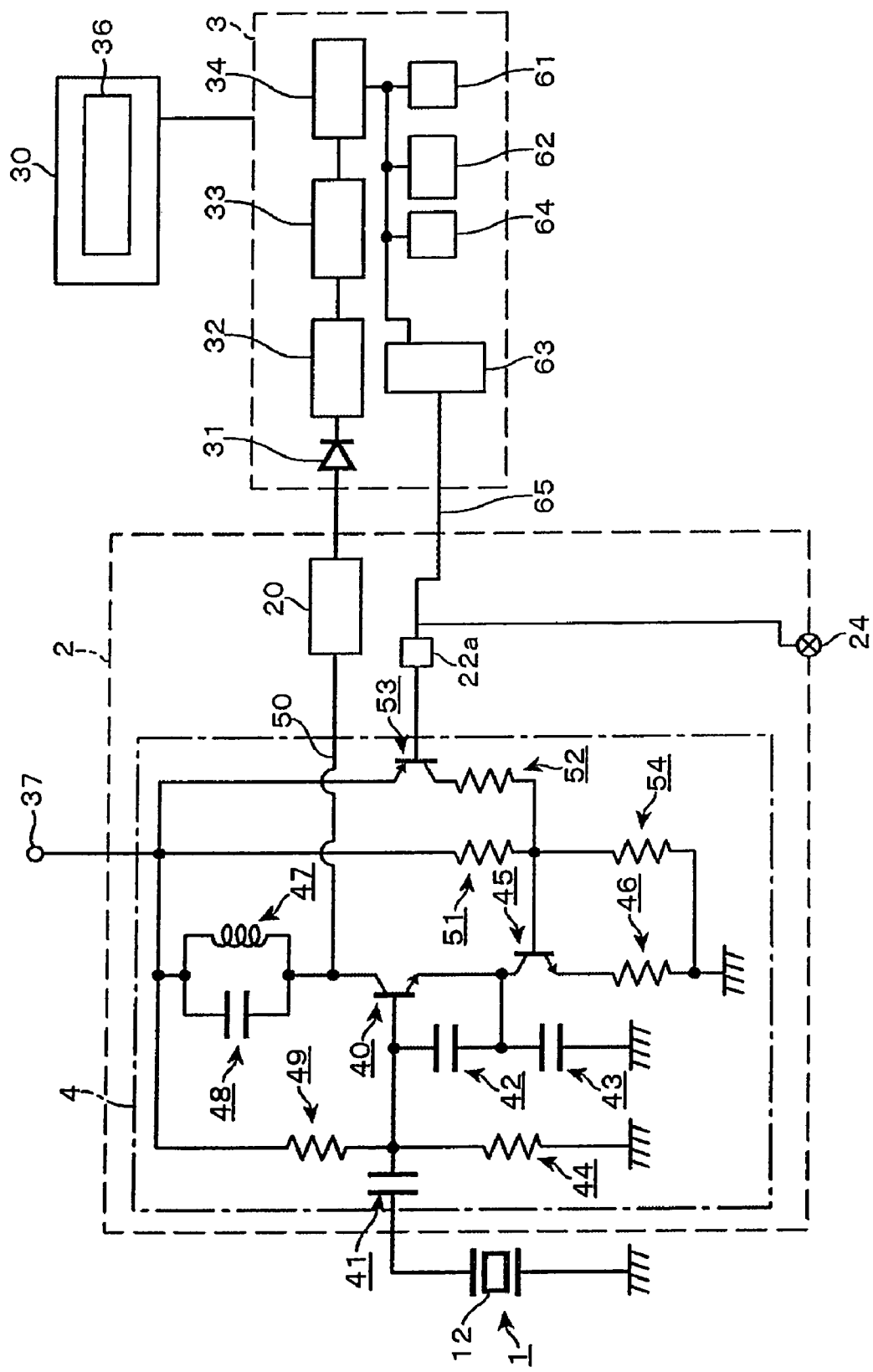
FIG. 4 is a plane view used to describe a sensing device of a second embodiment.

In a second embodiment, instead of the connection detecting part 21 and the one-shot circuit 22 provided in the oscillator circuit unit 2, a program causing the output of a pulse with a preset pulse width (time) when the connection of a quartz-crystal resonator 12 is detected is provided in a measuring part 3. This program, as functionally shown in FIG. 4, includes: a determining part 61, which corresponds to a connection detecting part, determining whether or not a frequency signal whose amplitude is a certain level or more has been input from an oscillator circuit unit 2; and a pulse outputting part 63 outputting a pulse for a period of time set by a timer part 62, which serving as a time setting part, when the determination result is "YES". The program further has a function of putting up a flag 64 when the pulse is once output from the pulse outputting part 63, and erasing the flag 64 when the determining part 61 thereafter determines that the frequency signal has disappeared, that is, when the quartz-crystal resonator 12 is detached from the oscillator circuit unit 2. Note that, in FIG. 4, 65 denotes a dedicated line connecting a base of a third transistor 53 and the pulse outputting part 63 via an inverting circuit 22a. The other structure is the same as that of the sensing device of the first embodiment, and therefore, portions that are the same as or are corresponding to those of the first embodiment will be denoted by the same reference numerals and symbols.

In this sensing device, an aging process follows the following procedure. When the quartz-crystal resonator 12 is connected to an oscillator circuit 4 and the frequency signal of the oscillator circuit 4 is input to a FGPA 33 via a buffer amplifier 20, a diode 31, and an A/D converter circuit 32, a CPU 34 detects a rising edge of input level of the frequency signal input by the determining part 61 and confirms the flag 64 at a point in time when the level exceeds a predetermined value. Then, when confirming that the flag 64 has logic "0", the CPU 34 determines that a current state is a state immediately after the quartz-crystal sensor 1 is connected, that is, a state where the aging process is not underway, to start the aging process. When the flag 64 has logic "1", it is determined that the aging process has been completed, and no aging process is performed.

When the aging process is started, the CPU 34 first transmits an activation command to the pulse outputting part 63 and the timer part 62, so that the pulse outputting part 63 supplies a pulse with a preset length to a base of a third transistor 53 via the inverting circuit 22a and at the same time, the timer part 62 starts counting the processing time. Further, the CPU 34 transmits count information of the timer part 62 to a control PC 30, and a control program 36 of the control PC 30 displays the count information on a display 39 (see FIG. 1).

When the pulse is output from the pulse outputting part 63 to the base of the third transistor 53, a red LED 24 of the oscillator circuit unit 2 is lighted, and high power is supplied to the quartz-crystal resonator 12, followed by the aging process as in the first embodiment. Further, while the aging process is underway, the CPU 34 transmits the count information of the timer part 62 to the control PC 30, and the control program 36 of the control PC 30 displays the count information on the display 39 (see FIG. 1).

When the count of the timer part 62 thereafter indicates a processing end time, the CPU 34 transmits a stop command to the pulse outputting part 63 and resets the count of the timer part 62. Thereafter, in the oscillator circuit unit 2, the red LED 24 is lighted out since the output of the pulse from the pulse outputting part 63 is stopped, and supply power to the quartz-crystal resonator 12 comes to have a value set at a regular time. Further, the CPU 34 transmits stop information of the timer part 62 to the control PC 30 and at the same time changes the value of the flag 64 to 1, and the control program 36 displays the end of the aging process on the display 39. Thereafter, the processing for the substance to be sensed is performed, similarly to the first embodiment.

In such a sensing device, as in the first embodiment, the oscillator circuit 4 including a series circuit of a resistor 52 and the third transistor 53 of PNP type also serves as an intense excitation circuit, and upon detecting the connection of the quartz-crystal sensor 1 to the oscillator circuit unit 2, forcibly gives a great mechanical vibration to the quartz-crystal resonator 12 by supplying the high power to the quartz-crystal resonator 12, thereby enabling the promotion of the disappearance of the distortion and stress of the quartz-crystal resonator 12. This makes it possible to reduce the time required for the aging process of the quartz-crystal resonator 12 to improve work efficiency.

[Third Embodiment]

Figure 5:
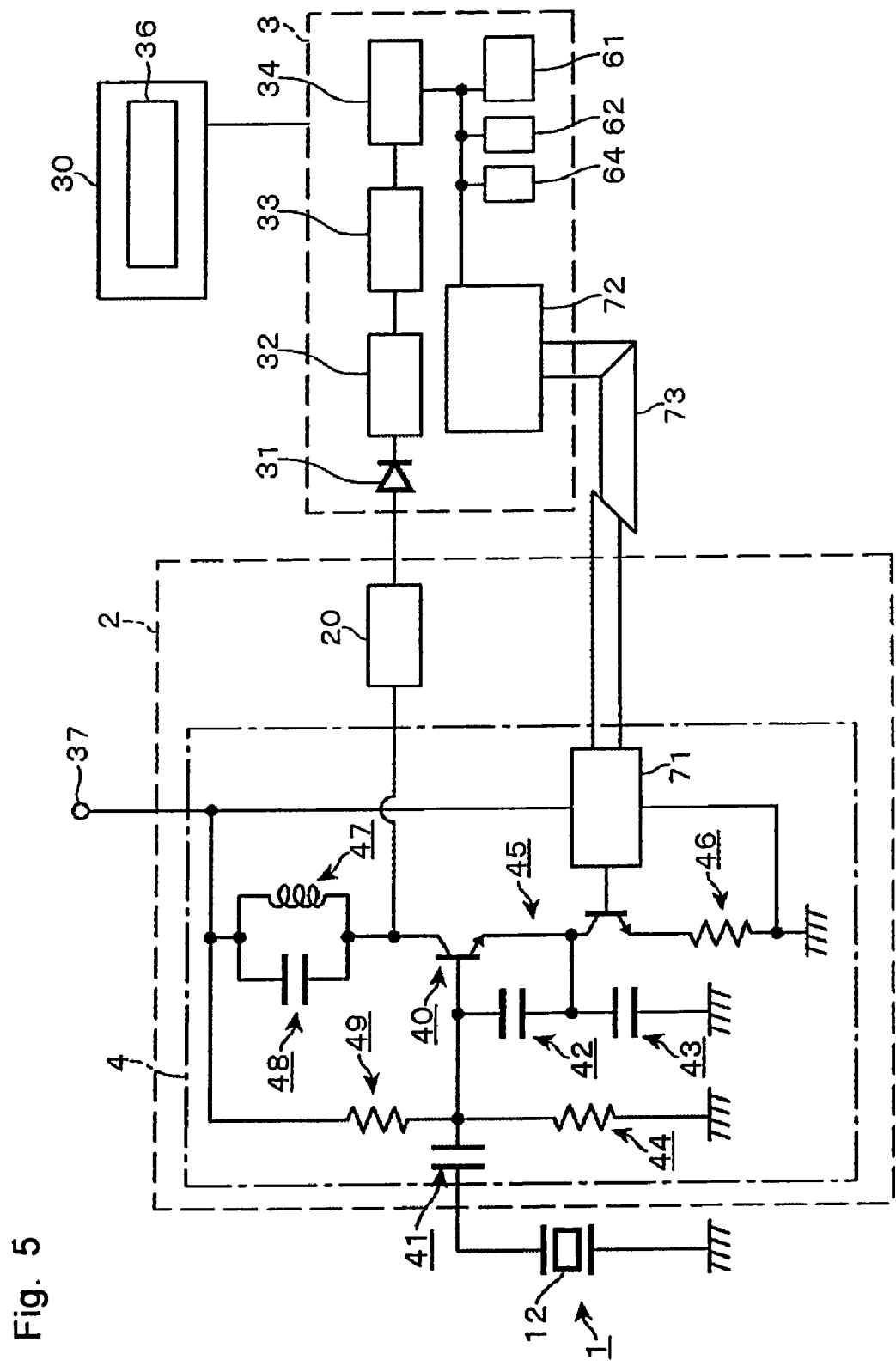
FIG. 5 is a plane view used to describe a sensing device of a third embodiment.

In a third embodiment, instead of the inverting circuit 22a, the third transistor 53, the series resistors 51, 54, and the resistor 52 provided in the oscillator circuit unit 2 in the second embodiment, a D/A converter circuit 71, which corresponds to a switch part, outputting a pulse to a base of a second transistor 45 is provided in an oscillator circuit 4, and instead of the pulse outputting part 63 provided in the measuring part 3 in the second embodiment, a control signal transmitting part 72 transmitting a digital control signal to the D/A converter circuit 71 based on a command from a CPU 34 is provided in a measuring part 3, as shown in FIG. 5. Upon receiving the digital control signal from the CPU 34 via the control signal transmitting part 72, the D/A converter circuit 71 converts the control signal into an analog signal and outputs the pulse based on the analog signal to a base of a second transistor 45. Note that, in FIG. 5, 73 denotes a parallel cable which connects the D/A converter circuit 71 and the control signal transmitting part 73 and is one of communication cables enabling high-speed data communication. The other structure is the same as that of the sensing device of the second embodiment, and therefore, portions that are the same as or are corresponding to those of the second embodiment will be denoted by the same reference numerals and symbols.

When an aging process is to be performed in this sensing device, a determining part 61 detects a rising edge of input level of an input frequency signal to confirm a flag 64 at a point in time when the level exceeds a predetermined value, similarly to the second embodiment. When it is confirmed that the flag 64 has logic "0", it is determined that a current state is a state immediately after a quartz-crystal sensor 1 is connected, that is, a state where the aging process is not underway, and the aging process is started.

When the aging process is started, the CPU 34 transmits the digital control signal to the D/A converter circuit 71 via the control signal transmitting part 72, the digital control signal being intended to cause the D/A converter circuit 71 to output the pulse for increasing a base potential of a second transistor 45 to the second transistor 45. Further, the CPU 34 transmits count information of a timer part 62 to a control PC 30, and a control program 36 of the control PC 30 displays the count information on a display 39 (see FIG. 1).

The D/A converter circuit 71 receiving the control signal converts the digital control signal to the analog control signal and outputs the pulse based on the control signal to the base of the second transistor 45. This as a result causes an increase in a base potential of the second transistor 45, and accordingly an increase in a base-emitter voltage of a first transistor 40, so that high power is supplied to a quartz-crystal resonator 12 and the aging process is performed, as in the first and second embodiments.

When the count of the timer part 62 thereafter indicates a processing end time, the CPU 34 transmits a digital control signal to the D/A converter circuit 71 via the control signal transmitting part 72, the digital control signal being intended to cause the D/A converter circuit 71 to output a pulse for increasing the base potential of the second transistor 45 to the second transistor 45. Consequently, the D/A converter circuit 71 outputs the pulse for returning the base potential of the second transistor 45 to the original state, so that the supply power to the quartz-crystal resonator 12 comes to have a value set at a regular time. Further, the CPU 34 transmits stop information of the timer part 62 to the control PC 30 and at the same time changes a value of the flag 64 to 1, and the control program 36 displays the end of the aging process on the display 39. Thereafter, the processing of a substance to be sensed is performed, similarly to the first embodiment.

In such a sensing device, the oscillator circuit 4 including the D/A converter circuit 71 serves as an intense excitation circuit, and upon detecting of the connection of the quartz-crystal sensor 1 to an oscillator circuit unit 2, forcibly gives a great mechanical vibration to the quartz-crystal resonator 12 by supplying the high power to the quartz-crystal resonator 12, so that the disappearance of the distortion and stress of the quartz-crystal resonator 12 is promoted. This can shorten the time required for the aging process of the quartz-crystal resonator 12 to improve work efficiency.

Incidentally, in the second and third embodiments, since the timer part 62 controls the processing time of the aging process, rewriting the timer part 62 makes it possible to change the period of time of the supply of the high power to the quartz-crystal resonator 12 in the aging process. Therefore, in this embodiment, only by rewiring the timer part 62, appropriate aging processes can be performed for different kinds of quartz-crystal resonators 12.

Further, in the second and third embodiments, the determining part 61, the timer part 62, and the flag 64 are incorporated in the measuring part 3, but as an embodiment of the present invention, these programs may be incorporated in the control program 36 of the control PC 30 and the command may be transmitted to the oscillator circuit unit 2 via the measuring part 3 from the control PC 30.

Further, in the second and third embodiments, the end of the aging process is determined based on the count by the timer part 62, but another alternative embodiment of the present invention may be, for example, that the control program monitors time-series data of the frequency signal transmitted from the measuring part, and the time until it is confirmed that the width of the amplitude of the frequency signal has a value falling within a permissible range set in advance is defined as the processing time, and the end command of the aging process is transmitted to the pulse outputting part or the control signal transmitting part when it is confirmed that this processing time has passed.

[Other Embodiment]

Figure 6:
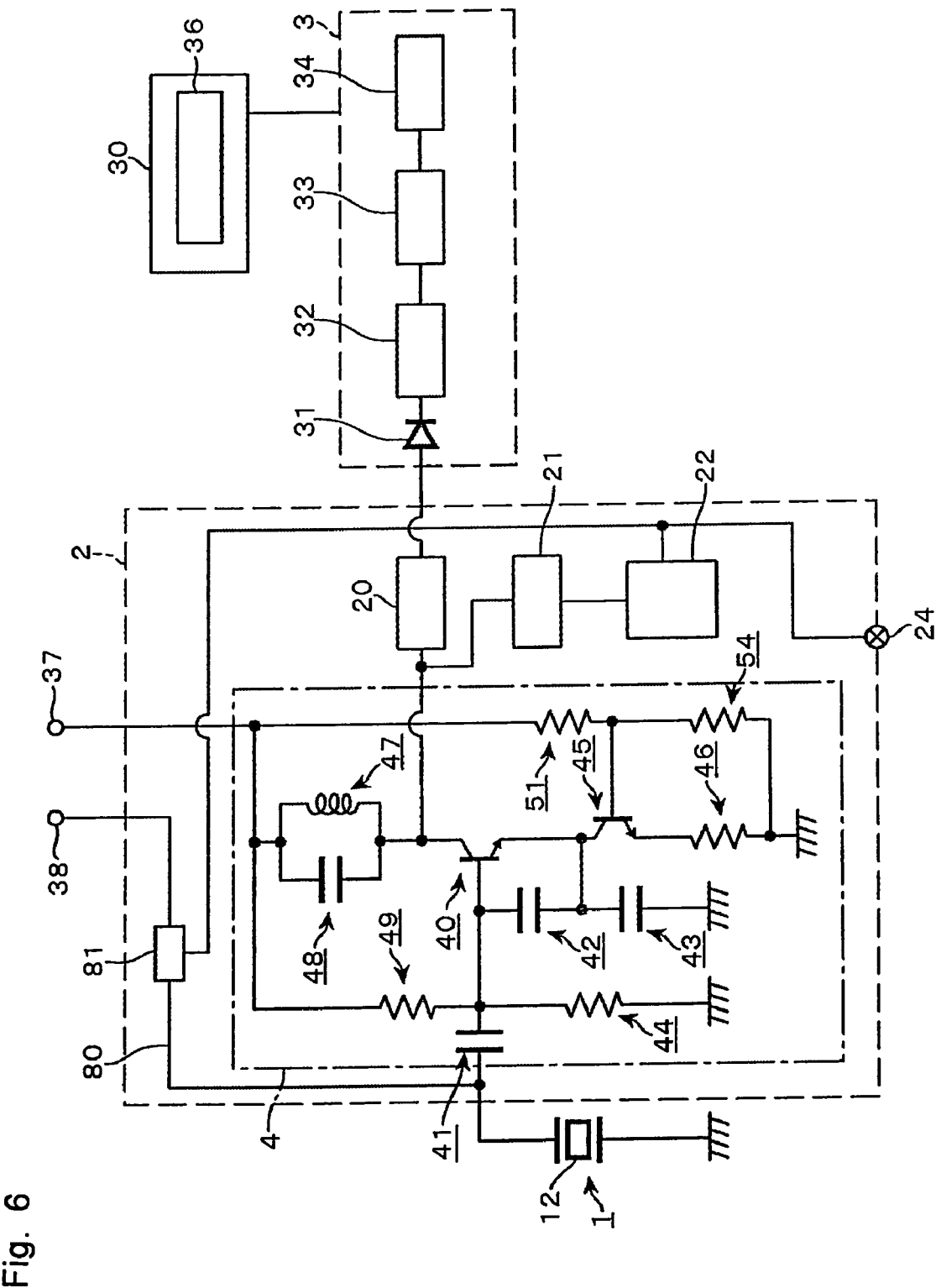
FIG. 6 is a plane view used to describe an oscillator circuit unit in a sensing device of another embodiment.

The sensing device of the present invention may be a sensing device shown next in FIG. 6. Instead of the resistor 52, the third transistor 53, and the inverting circuit 22a provided in the oscillator circuit 4 in the first embodiment, this sensing device includes: a power feeder 80 directly supplying a quartz-crystal sensor 1 with a current from an additional power source 38 provided separately from a power supply terminal 37; and a switching element 81 provided in the power feeder 80. The switching element 81 is connected to a one-shot circuit 22, and when a pulse is output from the one-shot circuit 22, a switch of the switching element 81 turns on so that the current is supplied to the quartz-crystal sensor 1 side. The other structure is the same as that of the sensing device of the first embodiment, and therefore, description thereof will be omitted.

In this sensing device, when a connection detecting part 21 detects that a quartz-crystal resonator 12 of the quartz-crystal sensor 1 is connected to an oscillator circuit 4 and the pulse is output from the one-shot circuit 22 to the switching element 81, the current is supplied from the additional power source 38 to the quartz-crystal sensor 1 side via the power feeder 80. This increases power supplied to the quartz-crystal resonator 12 to forcibly give a great mechanical vibration, which can promote the disappearance of the distortion and stress of the quartz-crystal resonator 12. Therefore, in such a sensing device, the power feeder 80 and the switching element 81 also serve as an intense excitation circuit and it is possible to shorten the preparation time required for the measurement of a substance to be sensed to improve work efficiency as in the above-described embodiments.

What is claimed is:

1. A sensing device which includes a piezoelectric resonator on whose surface an adsorption layer for adsorbing a substance to be sensed is formed and whose natural frequency changes when the substance to be sensed is adsorbed, and senses the substance to be sensed based on the natural frequency of the piezoelectric resonator, the sensing device comprising:
    an oscillator circuit oscillating the piezoelectric resonator;
    an intense excitation circuit intensely exciting the exciting the piezoelectric resonator connected to the oscillator circuit for a preset time period of time by supplying the piezoelectric resonator with high power equal to or more than twice regular power supplied at the time of the measurement of the substance to be sensed, to stabilize the oscillation of the piezoelectric resonator and
    a connection detecting part that detects the connection of the piezoelectric resonator to the oscillator circuit, and outputs a signal causing the intense excitation circuit to start an intense excitation operation.

2. The sensing device according to claim 1, wherein:
    the oscillator circuit serves as part of the intense excitation circuit; and
    the intense excitation circuit includes a switch part connected to the oscillator circuit to the piezoelectric resonator between the regular power and the high power.

3. The sensing device according to claim 1, further comprising a time sensing part setting the period of time of the intense excitation of the piezoelectric resonator.

4. The sensing device according to claim 1, further comprising an operation screen part via which the sensing device is operated, wherein the time setting part is combined in the operation screen display part.

5. The sensing device according to claim 1, wherein the signal causing the intense excitation circuit to start an intense excitation operation is a pulse width corresponding to a preset time period.

6. A sensing device, which includes a piezoelectric resonator on whose surface an adsorption layer for adsorbing a substance to be sensed is formed and whose natural frequency changes when the substance to be sensed is adsorbed, and which senses the substance to be sensed based on the natural frequency of the piezoelectric resonator, the sensing device comprising:
    an oscillator circuit outputting an excitation signal to the piezoelectric resonator causing the piezoelectric resonator to oscillate;
    a connection detecting part that detects a connection between the piezoelectric resonator and the oscillator circuit for a sensing operation; and
    an intense excitation circuit, coupled to the oscillator circuit; and
    wherein said connection detecting part upon said connection detection outputs a trigger signal causing the intense excitation circuit to start an intense excitation operation;
    wherein the intense excitation circuit in response to said trigger signal detects the excitation signal and in response provides to the oscillation circuit a pulse of preset duration for shortening a time for stabilizing the oscillation frequency of the piezoelectric resonator, said pulse causing the oscillator circuit to change power output of said excitation signal for the preset duration from a first power level to a second power level that is as least double the first power level, said oscillator circuit resuming power output at the first power level after said preset duration of said pulse.

* * * * *